United States Patent [19]

Mishima et al.

[11] Patent Number: 5,182,193
[45] Date of Patent: Jan. 26, 1993

[54] METHOD FOR MEASURING BIOMASS

[75] Inventors: Ken Mishima, Toyonaka; Akio Mimura, Fuji; Yoshimasa Takahara, Narashino; Kouji Asami, Kyoto; Tetsuya Hanai, Uji, all of Japan

[73] Assignee: Kabushiki Kaisha Kobe Seiko Sho, Kobe, Japan

[21] Appl. No.: 790,071

[22] Filed: Nov. 12, 1991

Related U.S. Application Data

[63] Continuation of Ser. No. 150,047, Jan. 29, 1988, abandoned.

[30] Foreign Application Priority Data

| Feb. 4, 1987 | [JP] | Japan | 62-22481 |
| Sep. 9, 1987 | [JP] | Japan | 62-224018 |
| Nov. 6, 1987 | [JP] | Japan | 62-279060 |

[51] Int. Cl.$^5$ ............................................. C12Q 1/02
[52] U.S. Cl. .................................. 435/29; 435/240.2; 435/240.4
[58] Field of Search ................................................ 435/29

[56] References Cited

U.S. PATENT DOCUMENTS

| 3,743,581 | 7/1973 | Cady et al. | 435/34 |
| 3,890,201 | 6/1975 | Cady | 435/34 X |
| 4,160,205 | 7/1979 | Hobbs et al. | 435/30 X |
| 4,204,037 | 5/1980 | Dill et al. | 435/34 X |
| 4,246,343 | 1/1981 | Wilkins et al. | 435/34 X |
| 4,264,728 | 4/1981 | Wilkins | 435/34 X |
| 4,758,509 | 7/1988 | Ottley | 435/39 X |
| 4,810,650 | 3/1989 | Kell et al. | 435/291 |

FOREIGN PATENT DOCUMENTS

| 2412165 | 9/1975 | Fed. Rep. of Germany . |
| 8802114 | 2/1988 | PCT Int'l Appl. . |
| 8802115 | 3/1988 | PCT Int'l Appl. . |
| 1032391 | 7/1983 | U.S.S.R. . |
| 1073676 | 2/1984 | U.S.S.R. . |
| 2136130 | 9/1984 | United Kingdom . |
| 2177801 | 1/1987 | United Kingdom . |
| 8600921 | 2/1986 | World Int. Prop. O. . |

OTHER PUBLICATIONS

*IEEE Trans. Biomed. Eng.*, BME-33, 242 (1986).
*Instrumental Methods for Rapid Microbiological Analysis*, 193 (1985).
K. Asami, et al, *J. Membrane Biol.*, 28, 169–180 (1976).
C. M. Harris, et al., *Bioelectrochemistry and Bioenergetics*, 11, 15–28 (1983).
Harris et al. *Biosensors*, 1, pp. 17 and 41–51 (1985).
Biological Abstracts, vol. 84, No. 12, Dec. 15, 1987, abstract No. 118090, Schaertel et al.
Biological Abstracts, vol. 84, No. 5, Sep. 1, 1987, abstract No. 45568, Nienwenhof et al.
Enzyme Microb Technol, 9(3), pp. 181–186, 1987.

*Primary Examiner*—Sam Rosen
*Attorney, Agent, or Firm*—Oblon, Spivak, McClelland, Maier & Neustadt

[57] ABSTRACT

A method for measuring a biomass which comprises measuring an electric capacitance across at least one pair of electrodes attached to a bioreactor, and thereby continuously measuring a biomass of organisms (such as microorganism and plant or animal cells), which may or may not be immobilized in the bioreactor, according to the electric capacitance (dielectric permitivity) measured. The present invention permits one to measure on-line the quantities of microorgansims or plant or animal cells without having to take samples from a bioreactor or culture tank.

5 Claims, 5 Drawing Sheets

METHOD FOR MEASURING BIOMASS

This application is a continuation of application Ser. No. 07/150,047, filed on Jan. 29, 1988, now abandoned.

BACKGROUND OF THE INVENTION

1. Field of the Invention

The present invention relates to a method for measuring biomass. More particularly, it relates to a method for measuring on-line the quantities of microorganisms or the quantities of animal or plant cells in a bioreactor. Thus the present invention will play an important role in bioindustry and microbial industry relating to medicine, food, sewage disposal, etc.

2. Description of the Prior Art

The bioreactor to produce useful substances by the aid of microorganisms, animal or plant cells, etc. is different from the ordinary reactor containing catalyst in that the biomass in the reactor changes from time to time. Therefore, measuring the biomass is very important for the design and control of bioreactor. In the case of a bioreactor in which microorganisms are not immobilized on a support but suspended in the solution, it is possible to measure the quantities of the microorganisms by several methods. They include, for example, the measurement of turbidity with scattered light, the measurement of absorption spectrum by a double beam spectrometer, and the measurement of fine particles by a projecting light particle sensor.

These conventional measuring methods have some drawbacks. For example, the measurement of the concentration of microorganisms in activated sludge or industrial effluent, which is expressed in terms of MLSS (Mixed Liquor Suspended Solids), does not give an accurate number of microbial cells because sludge contains a variety of organic and inorganic matters in addition to microorganisms. It is also very difficult to separate microbial cells alone from sludge and measure their concentration. To approximate the value of MLSS to the concentration of microorganism, there has been proposed the measurement of MLVSS (Mixed Liquor Volatile Suspended Solids) in sludge. In actual, however, MLSS is still being used to denote the concentration of microorganisms in activated sludge because the measurement of MLVSS takes almost twice as much time as the measurement of MLSS.

For the measurement of MLSS, several methods have been developed; however, none of them are satisfactory. That is, the method that employs ultrasonic waves cannot be applied to a sample containing bubbles. The method that employs light is liable to errors when the measuring window is unclean and the sample solution is colored or bubbled, and it requires a complex measuring mechanism. The method that employs mechanical means or bubbles becomes paralyzed when foreign matters are encountered. For this reason, it is an actual practice to take a small sample and measure the dry weight of it by a complex procedure.

Other measuring methods are also used for plant cells and animal cells which have a larger volume than microorganisms and tend to form flocs. According to them, measurement is accomplished by weighing the dry weight, calculating the wet volume of cells, or counting the number of stained cells under a microscope. Whichever method may be used, it is necessary to take a sample of cells from the reactor or culture tank. This leads to the possibility of contamination with infectious microbes, and contamination often forces one to abandon an expensive culture medium. An additional disadvantage of these measuring methods is that the result of measurement such as the quantity of cells cannot be used for the on-line control of the culture equipment.

It is a recent common practice to increase the density of microorganisms in a bioreactor through their immobilization by chemical or physical means, thereby improving the efficiency of a bioreactor. A problem in this technical field is the fact that there is no method of measuring the quantity of immobilized microorganisms in a bioreactor without destroying the system at all. Instead of the direct method which is not available at present, the indirect methods as mentioned above are used for the microorganisms suspended in water after sampling from a bioreactor. Alternatively, the microorganisms sampled from a bioreactor are dried and their dry weight is measured. As long as such indirect methods are used, it is impossible to control a bioreactor on real time basis according to the results of measurements. Therefore, there has been a demand for the development of a new method for measuring on-line the quantities of microorganisms without interrupting a bioreactor.

SUMMARY OF THE INVENTION

With the foregoing in mind, the present inventors completed this invention to establish a method for rapidly and accurately measuring on-line the biomass such as microorganisms and animal or plant cells in a bioreactor. Accordingly, it is an object of the present invention to provide a method for measuring a biomass which comprises measuring an electric capacitance (dielectric permitivity) across at least one pair of electrodes attached to a bioreactor, and thereby continuously measuring a biomass of organisms in the bioreactor according to the electric capacitance (dielectric permitivity) measured.

DETAILED DESCRIPTION OF THE INVENTION AND PREFERRED EMBODIMENTS

Roughly speaking, a cell of a living organism is composed of cytoplasma containing a cell nucleus etc. and a cell membrane surrounding the cytoplasma. The cell membrane is composed mainly of lipids and hence it has a very high electric resistance. Therefore, a bioreactor is regarded as an oil/water emulsion system which is composed of an electrolyte (substrate containing ions) and oil droplets (microorganisms) dispersed therein. The emulsion system has been theoretically elucidated by Hanai et al. (See "Emarujon no Kagaku" (Science of Emulsion) [III] and "Chori Kagaku" (Science of Cooking), vol. 7, No. 1, 1974.) By the application of Hanai's theory, it is possible to analyze the state of oil in an oil/water emulsion (for example, the ratio of the volume occupied by oil).

With this background in mind, the present inventors conducted a series of experiments with microorganisms and animal and plant cells. It was found from the experiments that the electric capacitance at frequencies in a certain range increases in proportion to the biomass such as microorganisms and plant or animal cells.

It is usually an electric capacitance that is obtained by a measuring instrument; and it is impossible to obtain a dielectric permitivity directly. This is because an electric capacitance varies depending on the area and shape of electrodes in the measuring cell and the distance of electrodes. Nevertheless, it is possible to convert an electric capacitance into a dielectric permitivity if a cell constant is previously established. The following explains how to determine biomass according to an electric capacitance measured.

Before performing actual measurement, it is necessary to obtain the frequency characteristics of a bioreactor containing no microorganisms and animal and plant cells (collectively referred to as living organisms), because the electric capacitance is affected by the shape of electrodes and culture equipment and other factors. The actual electric capacitance is obtained by subtracting the thus obtained value from the value measured on a bioreactor containing living organisms. In the presence of living organisms, the electric capacitance increases over a broad frequency range from several kHz to several MHz, the range varying depending on the ion concentration in the given environment and the kind of objects to be measured. If a frequency at which the electric capacitance changes most according to biomass is previously established, it is possible to calculate a biomass from an electric capacitance measured. In addition, if a relationship between an electric capacitance and a biomass (dry weight, cell number, etc.) is previously established, it is possible to easily calculate a biomass from an electric capacitance. Thus, the method of the present invention permits one to measure a biomass on-line without having to sample living organisms to be measured.

Figure 1:
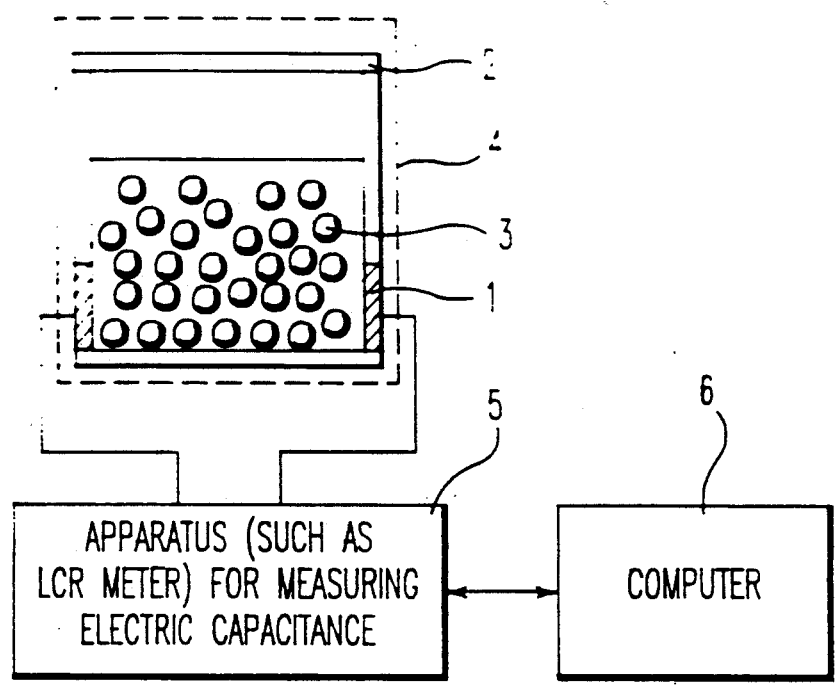
FIG. 1 is a schematic representation of an apparatus used to practice the method of the present invention.

According to the method of the present invention, the measurement of electric capacitance (dielectric permitivity) is accomplished by the aid of at least one pair of parallel electrodes attached to a culture tank (vessel) containing living organisms. A preferred measuring system is shown in FIG. 1. Referring to FIG. 1, there is shown a culture tank 2 which holds living organisms and has a pair of electrodes 1 (The living organism to be measured may be present in any state. For example, they may be immobilized, flocced, or suspended. These states may be present alone or in combination. Immobilization may be accomplished by entrapment or attachment. FIG. 1 shows an example of a culture tank filled with beads in which living organisms are immobilized.) The culture tank is enclosed by a shield 4 which is not essential but desirable. The electric capacitance is measured by the aid of an apparatus 5 (such as LCR meter) for measuring dielectric permitivity. The apparatus 5 may be of frequency-fixed type or frequency-variable type. It should preferably be one which is capable of measuring electric capacitance at a plurality of frequencies. The results of measurements may be converted into the value of biomass by manual calculations or by automatic calculations by a computer 6 connected to the apparatus. In the case where the living organisms or cells are in the form of suspension, measurement can be accomplished by placing the paired electrodes in the culture medium. The measuring method can also be applied to living organisms or cells immobilized in the usual way by the aid of an immobilizing agent such as polyacrylamide, polyacrylate, polystyrene, polyvinyl alcohol, photosensitive resin, and other resins; calcium alginate, κ-carrageenan, cellulose, dextran, and other polysaccharides; collagen and other proteins. The measuring method can also be applied to cells attached to or grown on the surface of plastics beads such as "Cytodex" produced by Pharmacia Co., Ltd. Incidentally, the apparatus for measuring electric capacitance is not limited to a specific type in the present invention.

EXAMPLE 1

The quantity of yeast immobilized with calcium alginate was measured dielectrically in the following manner. At first, an MY medium of the composition as shown in Table 1 was prepared, and 10 ml of the medium was placed in a test tube, followed by steam sterilization in the usual way.

TABLE 1

| Composition of MY Medium (pH 6.5) | |
| --- | --- |
| Yeast extract | 3 g |
| Malt extract | 3 g |
| Peptone | 5 g |
| Glucose | 10 g |
| Distilled water | 1000 ml |

The medium was inoculated with *Saccharomyces cerevisiae* IFO-0224 and standing culture was carried out at 28° C. for about 60 hours. The yeast was transplanted to 150 ml of separately prepared MY medium, and shaking culture was carried out for about 30 hours. The culture was collected by centrifugal separation (2000 rpm, 10 min). The yeast paste (2.5 ml) was diluted two-fold with the culture medium, and the dilution was mixed with 5 ml of 2% solution of sodium alginate. The mixture was added dropwise to a 0.1M solution of calcium chloride through an injection needle. Thus there were obtained beads of immobilized yeast. It was estimated that the beads contain 25% of yeast. In the same way as mentioned above, there were obtained four kinds of beads each containing 15%, 10%, 5%, and 2.5% of yeast. The thus prepared beads were treated with a 20 mM solution of calcium chloride cooled to 4° C. and then charged into an apparatus as shown in FIG. 1 for measurement.

Figure 2:
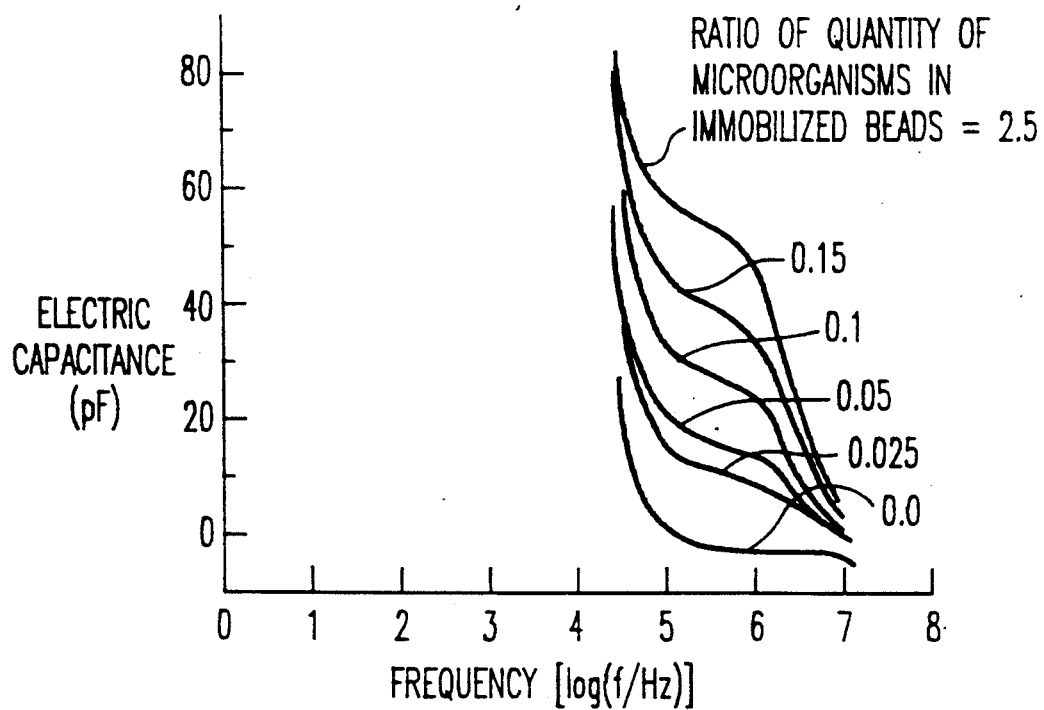
FIG. 2 is a graph showing the frequency characteristics of electric capacitance which are recorded at varied quantities of microorganisms immobilized in beads with calcium alginate.
Figure 3:
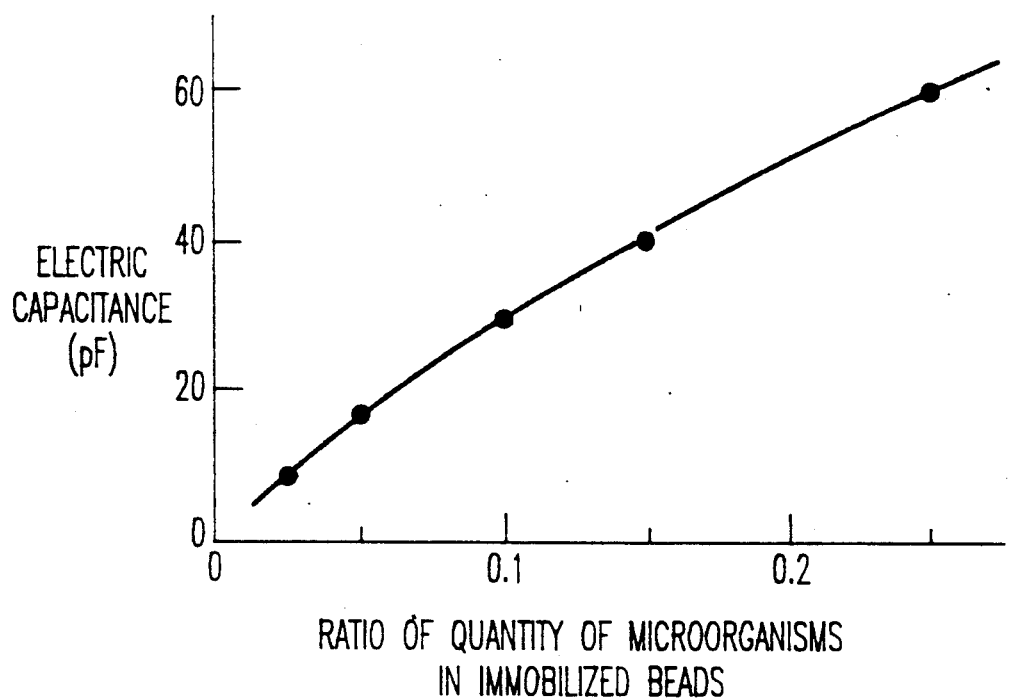
FIG. 3 is a graph showing the relationship between the electric capacitance and the quantities of yeast immobilized in beads with calcium alginate.

The electric capacitance of each sample (containing 2.5%, 5%, 10%, 15%, 25%, and 0% of yeast) was plotted by using a computer as shown in FIG. 2. The relationship between the quantity of yeast and the electric capacitance at a frequency of 300 kHz was obtained from FIG. 2, and the result is plotted as shown in FIG. 3. It is noted from FIG. 3 that there exists a close relationship between the quantity of yeast and the electric capacitance. This relationship makes it possible to measure the quantity of yeast by the electric capacitance.

EXAMPLE 2

The quantities of immobilized bacteria and fungi were measured dielectrically in the following manner. At first, glucose bouillon medium of the composition as shown in Table 2 was prepared, and the medium was inoculated with *Escherichia coli* IFO 3366, followed by shaking culture at 37° C. for 24 hours. The culture was collected for the subsequent experiment. The samples for measurement were prepared in the same manner as in Example 1.

TABLE 2

| Composition of Glucose Buoillon Medium (pH 6.5) | |
|---|---|
| Glucose | 10 g |
| Meat extract | 10 g |
| Peptone | 5 g |
| NaCl | 5 g |
| Distilled water | 1000 ml |

Separately, a potato dextrose medium of the composition as shown in Table 3 was prepared, and the medium was inoculated with Aspergillus oryzae IFO 4176, followed by shaking culture at 28° C. The culture was collected for the subsequent experiment. The samples for measurement were prepared in the same manner as in Example 1.

TABLE 3

| Potato Dextrose Medium (pH 5.5) | |
|---|---|
| Glucose | 20 20 g |
| Potato extract | 4 g |
| Distilled water | 1000 ml |

Immobilization in this example was carried out in the following three methods. (1) Immobilization with a photosensitive resin: A suspension of microorganisms was mixed with a photocurable resin solution (ENTG-3800), a photopolymerization initiator S, and a molding auxiliary (all made by Kansai Paint Co., Ltd.) in the ratio shown in Table 4. The resulting mixture was added dropwise to a 0.3M solution of calcium chloride through an injection needle, to yield beads containing microorganisms. The beads were transferred to a Petri dish and irradiated with ultraviolet rays for 5 minutes to give immobilized beads.

TABLE 4

| Formulation of Photosensitive Resin | |
|---|---|
| Photosensitive resin ENTG-3800 | 2 |
| Photopolymerization initiator S | 0.01 |
| Molding auxiliary A | 1 |
| Suspension of microorganisms | 1 |

(2) Immobilization with k-carrageenan was carried out in the usual way. (See A. Nguyan and J. H. Luong, Biotechnology and Bioengineering, vol. 28, pp. 1261–1267, 1986.) (3) Immobilization with polyacrylamide was carried out in the usual way. (See "Immobilized Enzyme", edited by Chibata, issued by Kodansha, Japan, 1975.)

Figure 4:
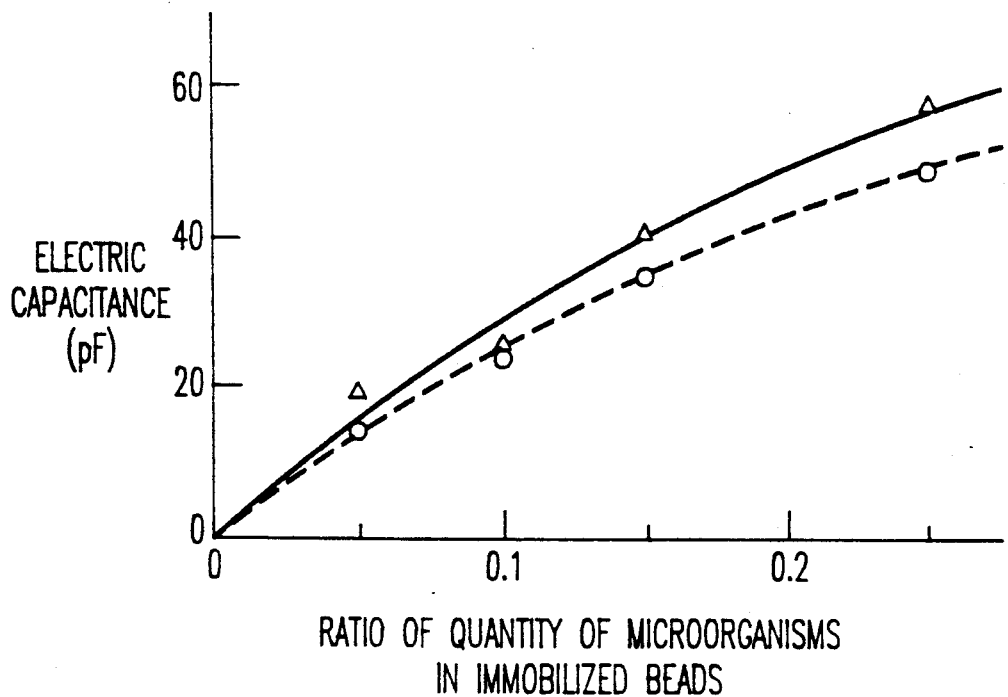
FIG. 4 is a graph showing the relationship between the electric capacitance and the quantities of *Escherichia coli* (◯) or the quantities of *Aspergillus oryzae* (△) immobilized in beads with calcium alginate.
Figure 5:
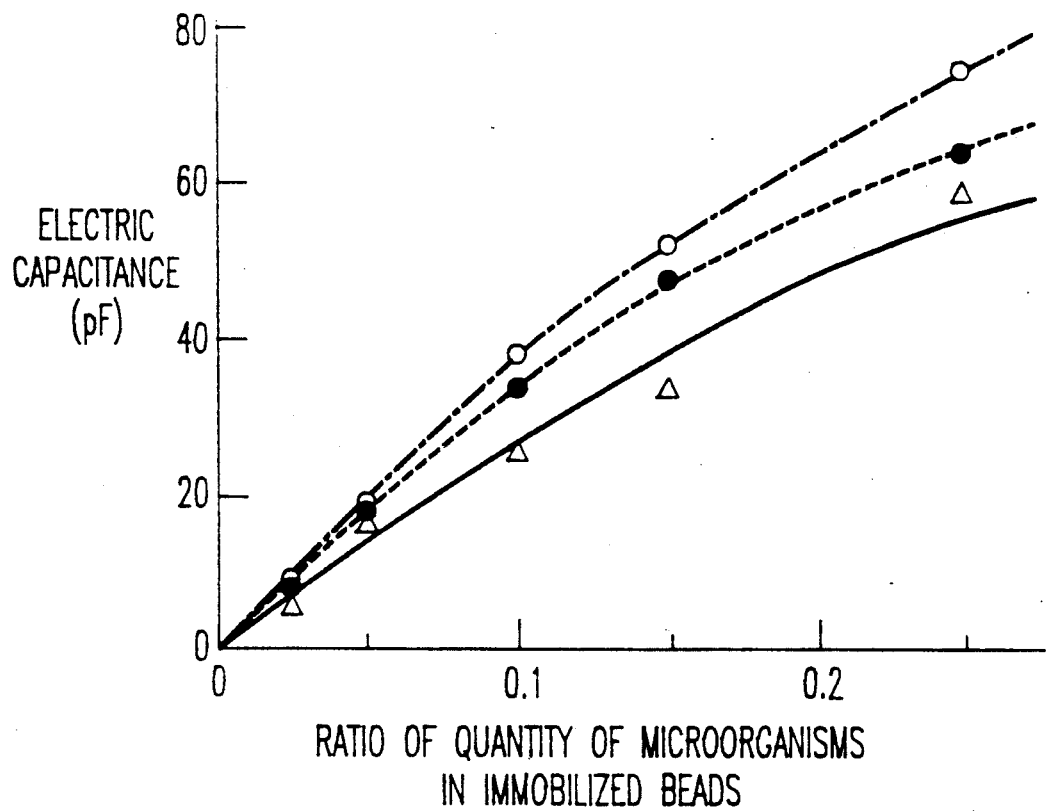
FIG. 5 is a graph showing the relationship between the electric capacitance of the quantities of yeast immobilized in beads with κ-carrageenan (△), polyacrylamide ( ), or photosensitive resin (◯).

FIG. 4 shows the results of experiments with bacteria and fungi immobilized with calcium alginate under the above-mentioned conditions. FIG. 5 shows the results of experiments with yeast immobilized with k-carrageenan, polyacrylamide, or photosensitive resin. It is noted from FIGS. 4 and 5 that there exists a close relationship between the quantity of microorganisms in the sample and the electric capacitance.

EXAMPLE 3

Figure 6:
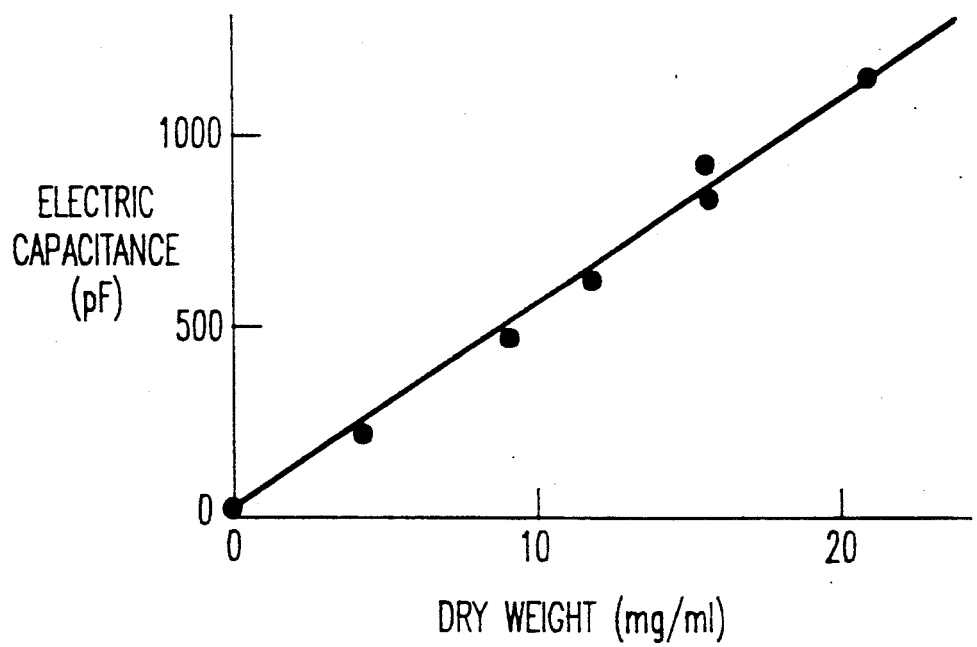
FIGS. 6 and 7 are graphs showing the relationship between the electric capacitance and the concentrations of plant cells and animal cells obtained in Example 3 and Example 4, respectively.

At first, there was prepared a basal medium of the composition as shown in Table 5 which is commonly used for propagation and culture of plant cells. (see "Manual for Plant Cell Culture", issued by Kodansha, Japan, 1984) To this basal medium were added $5 \times 10^{-5}$M of naphthalene acetic acid and $1 \times 10^{-5}$M of benzyladenine. The medium was dispensed in 100 ml portions into 500-ml Erlenmeyer flasks, followed by sterilization at 120° C. for 15 minutes. To the medium was transplanted 10 ml of previously cultured cells of Sesamum indicum L. The culture was carried out at 28° C. with stirring at 75 rpm under the light of 12,000 lux. After three weeks of cultivation, the medium containing cells was made into samples containing cells at different concentrations. Each sample was charged into a measuring apparatus as shown in FIG. 1 and the electric capacitance was measured. After that, the dry weight of each sample was measured. FIG. 6 shows the relationship between the quantity of plant cells (dry basis) and the electric capacitance at a frequency of 3 kHz. It is noted from FIG. 6 that there exists an almost linear relationship between the quantity of cells in the sample and the electric capacitance.

TABLE 5

| Ammonium nitrate | 1,650 mg |
|---|---|
| Potassium nitrate | 1,900 mg |
| Calcium chloride | 440 mg |
| Magnesium sulfate | 370 mg |
| Potassium dihydrogenphosphate | 170 mg |
| Boric acid | 6.2 mg |
| Manganese sulfate | 22.3 mg |
| Zinc sulfate | 8.6 mg |
| Potassium iodide | 0.83 mg |
| Sodium molybdate | 0.25 mg |
| Cobalt chloride | 0.025 mg |
| Copper sulfate | 0.025 mg |
| EDTA sodium salt | 37.3 mg |
| Ferrous sulfate | 27.8 mg |
| myo-Inositol | 100 mg |
| Glycine | 2 mg |
| Pyridoxine hydrochloride | 0.5 mg |
| Nicotinic acid | 0.5 mg |
| Thiamine hydrochloride | 0.1 mg |
| Sucrose | 30 g |
| Water | 1,000 ml |
| pH 5.7 | |

EXAMPLE 4

Figure 7:
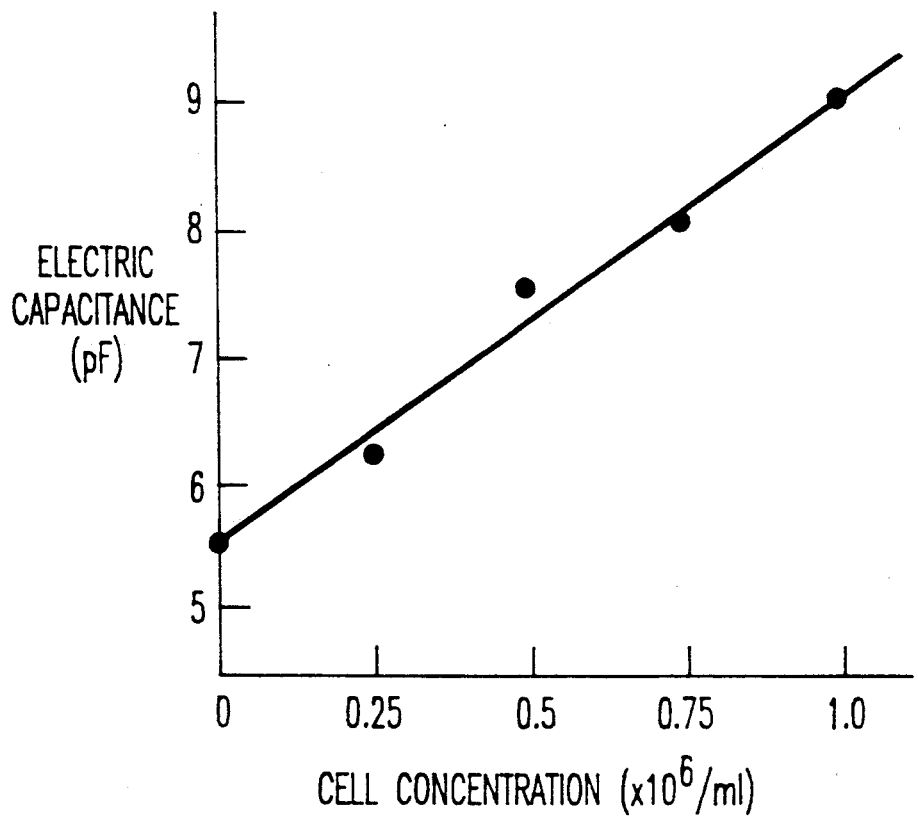

A cell strain (K-562) of myeloid leukemia of human origin was cultured according to the method commonly used for the culture of animal cells. (See "Manual for Cell Culture" issued by Kodansha.) A culture medium was prepared by adding 10% of fetal bovine serum to RPMI-1640 medium (made by Dainippon Pharmaceutical Co., Ltd., Japan) which is in general use. This culture medium was dispensed in 10 ml portions into plastics dishes, 10 cm in diameter, for cell culture. To the dispensed medium were transplanted the above-mentioned cells in a concentration of $1\times10^5$ cells per ml. Standing culture was carried out at 37° C. for 4 days in an incubator containing 5% of carbon dioxide gas. The cultured cells were collected by centrifugation at 1000 rpm. Samples in which the cultured cells are suspended at different concentrations were prepared. The electric capacitance of each sample was measured at a frequency of 100 kHz. After measurement, the number of cells in each sample was counted under a microscope by the aid of a Bürker-Türk hemocytometer. FIG. 7 shows the relationship between the electric capacitance and the number (concentration) of cells. It is noted from FIG. 7 that there exists an almost linear relationship between the number of cells in each culture medium and the electric capacitance.

EXAMPLE 5

Figure 8:
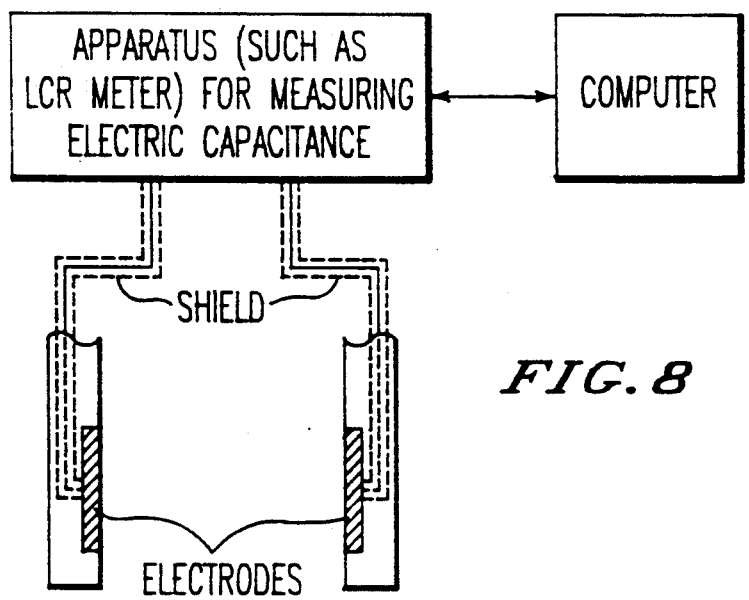
FIG. 8 is a schematic representation of an apparatus used to practice the method of the present invention.
Figure 9:
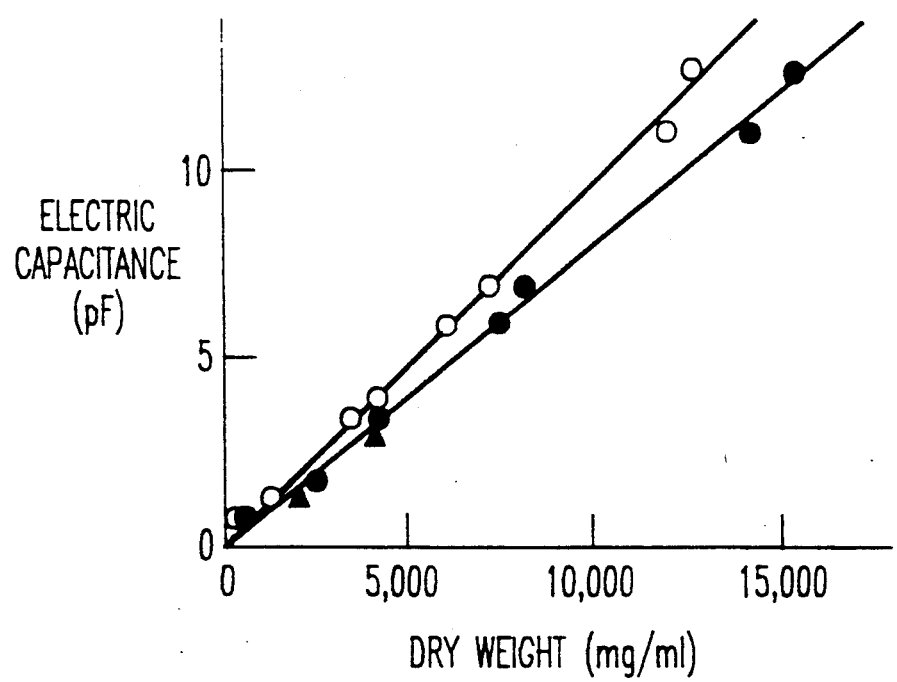
FIG. 9 is a graph showing the relationship between the difference of the electric capacitance at a frequency of 30 kHz and the electric capacitance at a frequency of 10 MHz and the MLSS (●) and MLVSS (◯) measured for the sludge collected from a sewage disposal plant. (The symbol ▲ represents the value measured in the aerated state.)

A liquid sample was taken from the aeration tank of a sewage disposal plant. After separation into precipitates and supernatant liquid, they were mixed again in different ratios to prepare samples each containing a different amount of suspended solids (SS). The electric capacitance of each sample was measured by immersing the electrodes as shown in FIG. 8 in the sample. For some samples, the electric capacitance was measured in the aerated state. The sample underwent washing with water and centrifugal precipitation (3000 rpm for 5 min) three times each for the removal of soluble matters and floating matters such as broken pieces of bacteria. MLSS and MLVSS were determined according to the sewage water testing method. FIG. 9 shows the relationship between SS (MLSS and MLVSS) and the electric capacitance expressed by the difference between the value measured at a frequency of 30 kHz and the value measured at a frequency of 10 MHz. It is noted from FIG. 8 that there exists an almost linear relationship between the quantity of bacteria in sludge and the electric capacitance.

EXAMPLE 6

Figure 10:
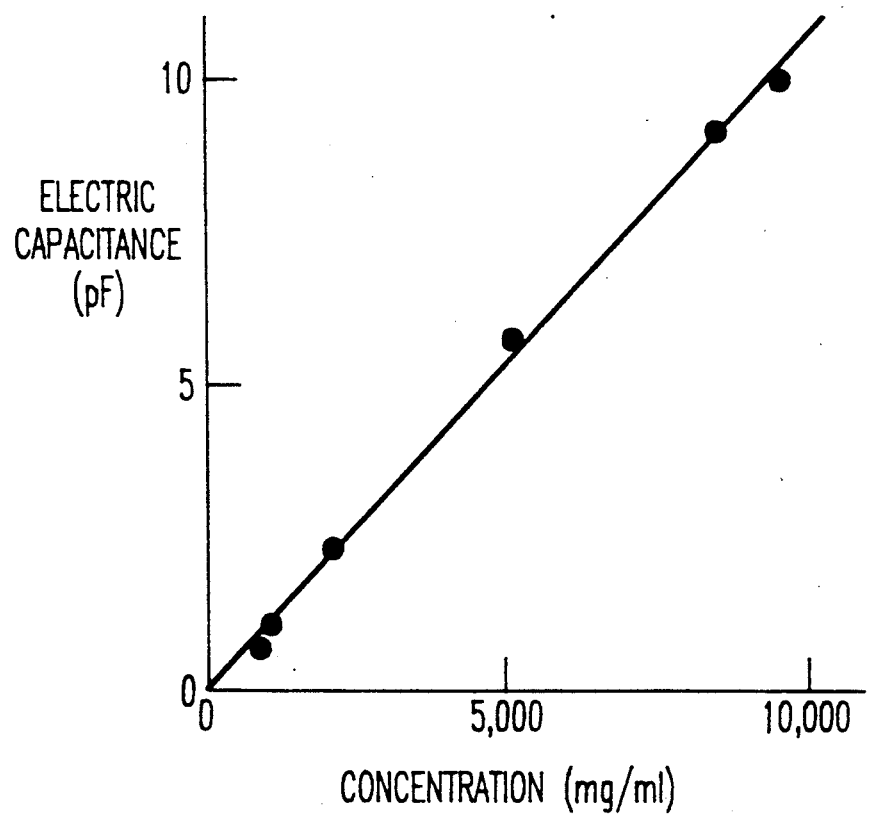
FIG. 10 is a graph showing the relationship between the electric capacitance and the MLSS in industrial effluent measured at a frequency of 30 kHz.

A liquid sample was taken from a sewage disposal plant for industrial effluent containing starch. After separation into precipitates and supernatant liquid, they were mixed again in different ratios to prepare two each of samples, each containing a different amount of suspended solids (SS). The electric capacitance (at 30 kHz) of one set of samples was measured by immersing the electrodes as shown in FIG. 8 in the sample. The same procedure was repeated for the same set of samples after the cell membrane of the bacteria was destroyed by a hydrolase. The difference of the two values was obtained. The other set of samples underwent washing with water and centrifugal precipitation (3000 rpm for 5 min) three times each. MLSS was determined according to the sewage water testing method. FIG. 10 shows the relationship between MLSS and the electric capacitance measured at a frequency of 30 kHz. It is noted from FIG. 10 that three exists an almost linear relationship between the quantity of bacteria in sludge and the electric capacitance.

As mentioned above, the present invention has made it possible for the first time to measure the biomass of microorganisms and animal and plant cells, which could not be measured by the conventional method without destroying the system, on account of its entirely new idea of measuring the electric capacitance. In other words, the present invention permits one to measure on-line the quantities of microorganisms, animal cells or plant cells without having to take samples from a bioreactor or culture tank. Because of its capability to measure the quantities of microorganisms, animal or plant cells without destroying them, the method of the present invention will find general use in biotechnology, vaccine manufacturing, experiments with microorganisms, animal or plant cells, and many other fields.

What is claimed is:

1. A method for determining a biomass of organisms, which comprises:
    measuring an electric capacitance at a frequency of 100 kHz to 10 MHz across at least one pair of electrodes installed in a bioreactor, and
    determining, according to the electric capacitance measured, the biomass of organisms in the bioreactor by a predetermined relationship between the biomass and the electric capacitance.

2. A method for measuring a biomass as claimed in claim 1, wherein the organisms are microorganisms.

3. A method for measuring a biomas as claimed in claim 1, wherein the organisms are plant cells.

4. A method for measuring a biomass as claimed in claim 1, wherein the organisms are animal cells.

5. A method for measuring a biomass as claimed in any of claims 1, 2, 3 or 4, wherein the organisms are those which are immobilized in the bioreactor.

* * * * *